US010765753B2

(12) United States Patent
Lee et al.

(10) Patent No.: US 10,765,753 B2
(45) Date of Patent: Sep. 8, 2020

(54) POLYMER NANOPARTICLE FREEZE-DRIED PRODUCT, AND PREPARATION METHOD THEREFOR

(71) Applicant: SAMYANG BIOPHARMACEUTICALS CORPORATION, Seoul (KR)

(72) Inventors: Sa Won Lee, Daejeon (KR); Gyeong Hae Kim, Daejeon (KR); Min Hyo Seo, Daejeon (KR)

(73) Assignee: SAMYANG BIOPHARMACEUTICALS CORPORATION, Seoul (KR)

( * ) Notice: Subject to any disclaimer, the term of this patent is extended or adjusted under 35 U.S.C. 154(b) by 0 days.

(21) Appl. No.: 15/540,674

(22) PCT Filed: Dec. 28, 2015

(86) PCT No.: PCT/KR2015/014318
§ 371 (c)(1),
(2) Date: Jun. 29, 2017

(87) PCT Pub. No.: WO2016/108534
PCT Pub. Date: Jul. 7, 2016

(65) Prior Publication Data
US 2018/0000946 A1 Jan. 4, 2018

(30) Foreign Application Priority Data

Dec. 30, 2014 (KR) ........................ 10-2014-0194156

(51) Int. Cl.
A61K 47/34 (2017.01)
A61K 9/19 (2006.01)
C08G 63/06 (2006.01)
C08K 3/10 (2018.01)
C08K 3/16 (2006.01)
A61K 9/08 (2006.01)
A61K 31/506 (2006.01)
A61K 47/26 (2006.01)
A61K 31/337 (2006.01)
A61K 9/51 (2006.01)
C08K 3/22 (2006.01)

(52) U.S. Cl.
CPC ............... A61K 47/34 (2013.01); A61K 9/08 (2013.01); A61K 9/19 (2013.01); A61K 9/5146 (2013.01); A61K 9/5153 (2013.01); A61K 31/337 (2013.01); A61K 31/506 (2013.01); A61K 47/26 (2013.01); C08G 63/06 (2013.01); C08K 3/10 (2013.01); C08K 2003/162 (2013.01); C08K 2003/2206 (2013.01)

(58) Field of Classification Search
CPC . A61K 47/34; A61K 9/08; A61K 9/19; A61K 9/5146; A61K 9/5153; A61K 31/337; A61K 31/506; A61K 47/26; C08G 63/06
See application file for complete search history.

(56) References Cited

U.S. PATENT DOCUMENTS

| 7,879,317 | B2 * | 2/2011 | Seo et al. |
| 2003/0143184 | A1 | 7/2003 | Seo et al. |
| 2004/0253315 | A1 | 12/2004 | Ogawa et al. |
| 2005/0201972 | A1 | 9/2005 | Seo et al. |
| 2005/0226893 | A1 | 10/2005 | Juneau et al. |
| 2008/0213215 | A1 * | 9/2008 | Krishnan |
| 2008/0260850 | A1 * | 10/2008 | Yi |
| 2009/0036389 | A1 | 2/2009 | Kwon et al. |
| 2010/0286075 | A1 | 11/2010 | Lee et al. |
| 2011/0224151 | A1 | 9/2011 | Kang et al. |
| 2011/0263481 | A1 | 10/2011 | Seo et al. |
| 2014/0199286 | A1 | 7/2014 | Zhao et al. |

FOREIGN PATENT DOCUMENTS

| JP | 2007-526329 A | 9/2007 |
| JP | 2008-231067 A | 7/2009 |
| KR | 10-2001-0105239 A | 11/2001 |
| KR | 10-2003-0045611 A | 6/2003 |
| KR | 10-2004-0018432 A | 3/2004 |
| KR | 10-2006-0013377 A | 2/2006 |
| KR | 10-2009-0049239 A | 5/2009 |
| KR | 10-2009-0073970 A | 7/2009 |

(Continued)

OTHER PUBLICATIONS

Chemical Book data on doxorubicin hydrochloride (https://www.chemicalbook.com/ChemicalProductProperty_EN_CB0110633.htm, pp. 1-8, accessed Jan. 28, 2019) (Year: 2019).*
Abdelwahed et al, "Freeze-drying of nanoparticles: Formulation, process and storage considerations", Advanced Drug Delivery Reviews, Oct. 6, 2006, vol. 58, No. 15, pp. 1688-1713.
International Search Report for PCT/KR2015/014318 dated Apr. 11, 2016.
Extended European Search Report, dated Jul. 17, 2018, for European Application No. 15875628.8.

(Continued)

Primary Examiner — Alma Pipic
(74) Attorney, Agent, or Firm — Birch, Stewart, Kolasch & Birch, LLP

(57) ABSTRACT

The present invention relates to a polymer nanoparticle freeze-dried product, and a preparation method therefor, the polymer nanoparticle freeze-dried product being obtainable by treating, through a freeze-drying process comprising an annealing step, a polymer nanoparticle aqueous solution comprising an amphiphilic block copolymer, a polylactic acid derivative having a carboxyl terminal group, and a freeze-drying adjuvant, wherein the polymer nanoparticle freeze-dried product is reconstituted within five minutes upon reconstitution by means of an aqueous solvent under atmospheric pressure.

10 Claims, 5 Drawing Sheets

(56) References Cited

FOREIGN PATENT DOCUMENTS

| WO | WO 03/005992 A1 | 1/2003 |
| WO | WO 2010/074380 A1 | 7/2010 |

OTHER PUBLICATIONS

Ishihara et al., "Preparation and characterization of a nanoparticulate formulation composed of PEG-PLA and PLA as anti-inflammatory agents," International Journal of Pharmaceutics, Elsevier, NL, vol. 385, No. 1-2, XP026814035, Jan. 29, 2010, pp. 170-175.

\* cited by examiner

[Figure 1]
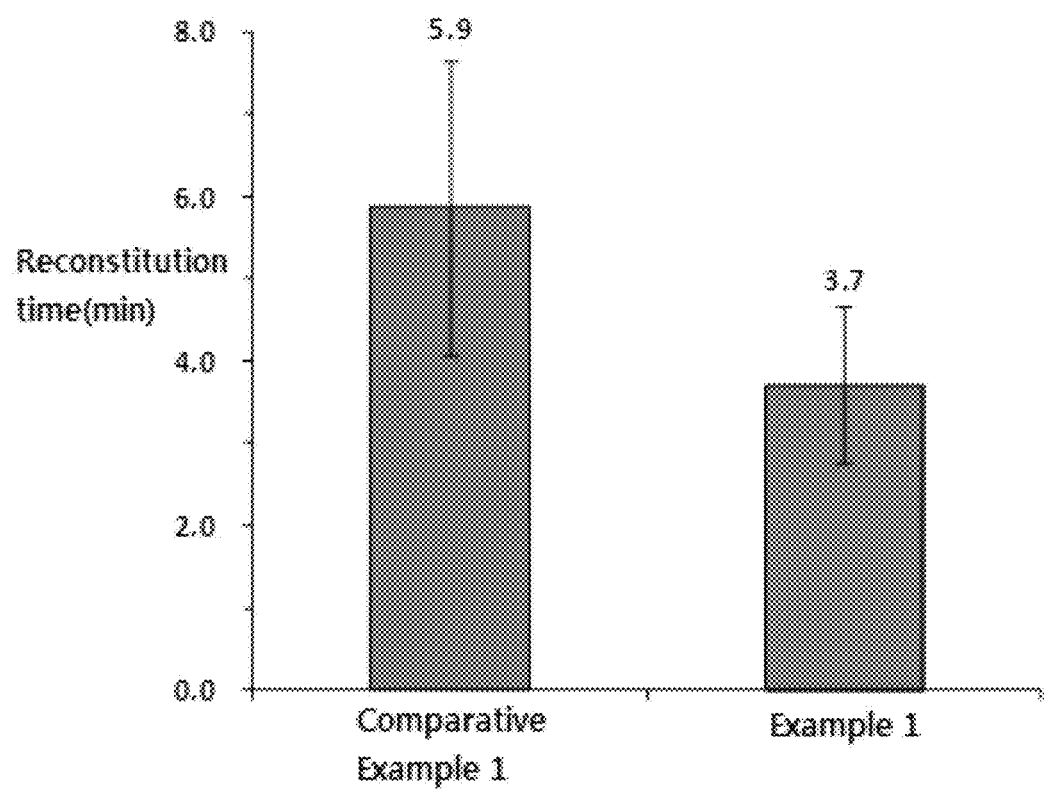

[Figure 2]
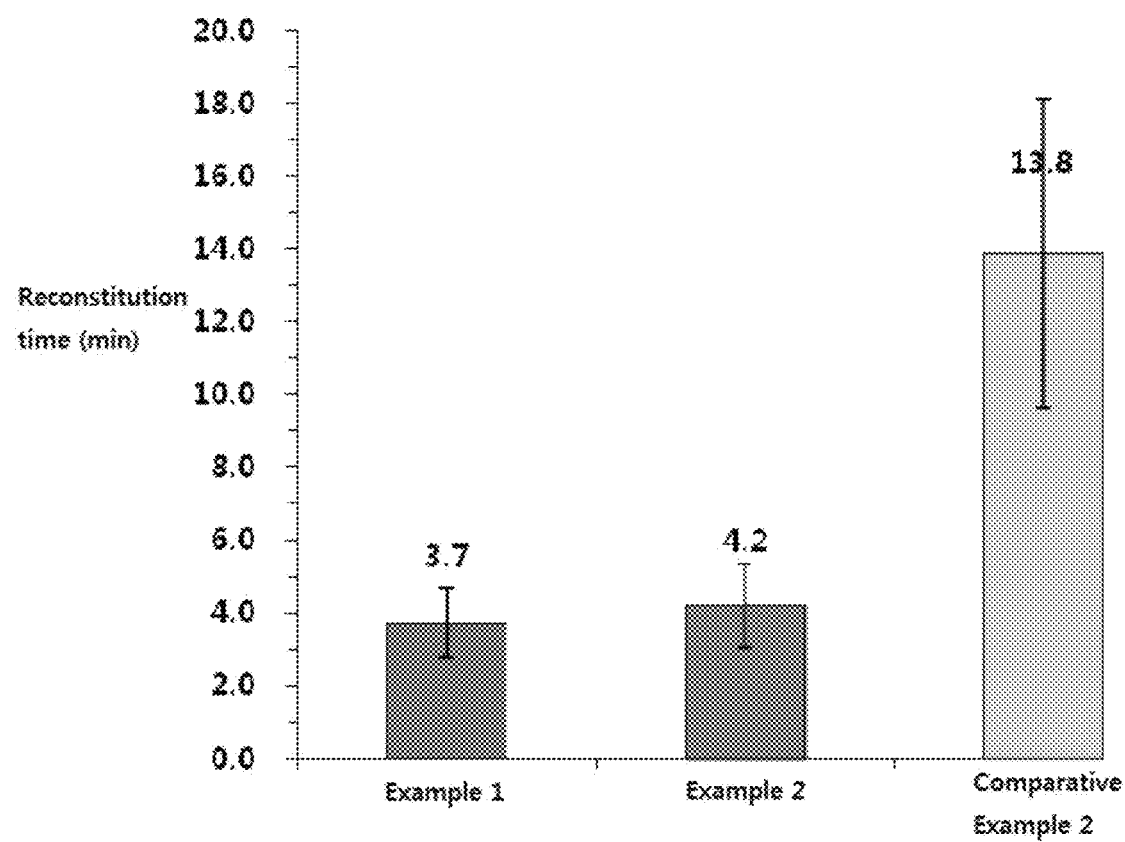

[Figure 3]
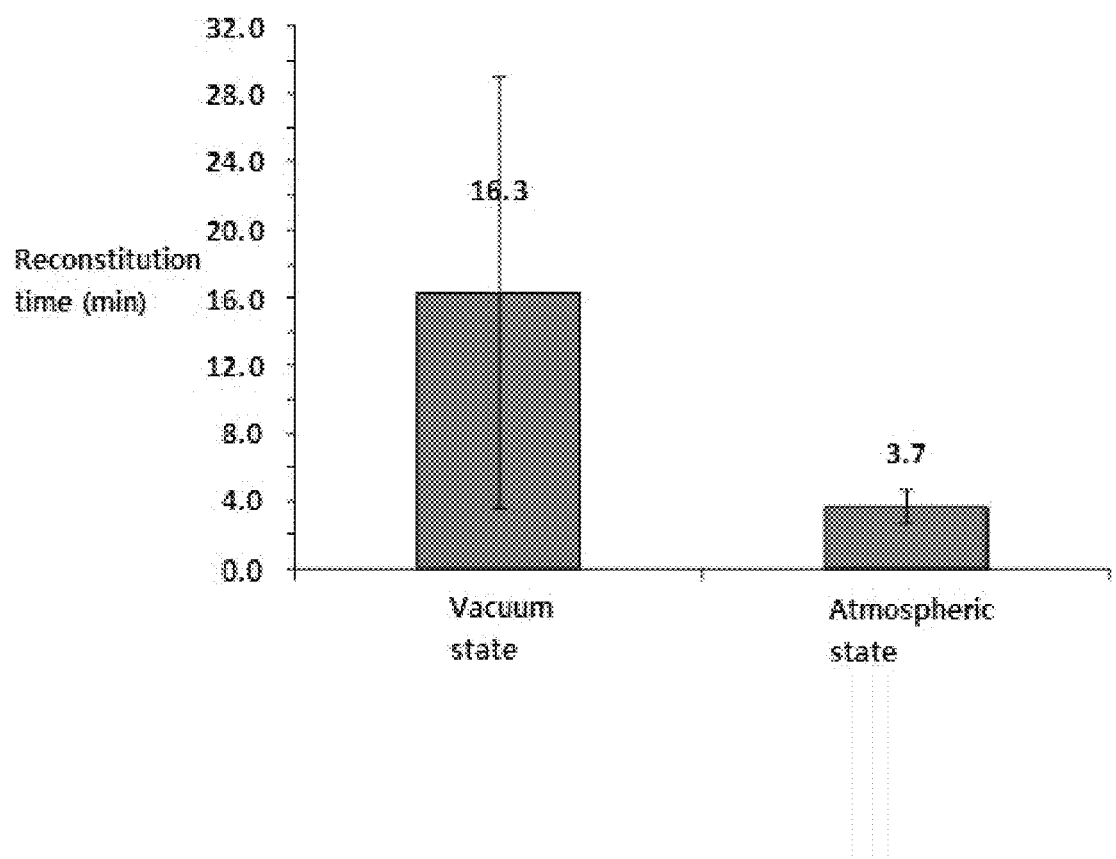

[Figure 4]
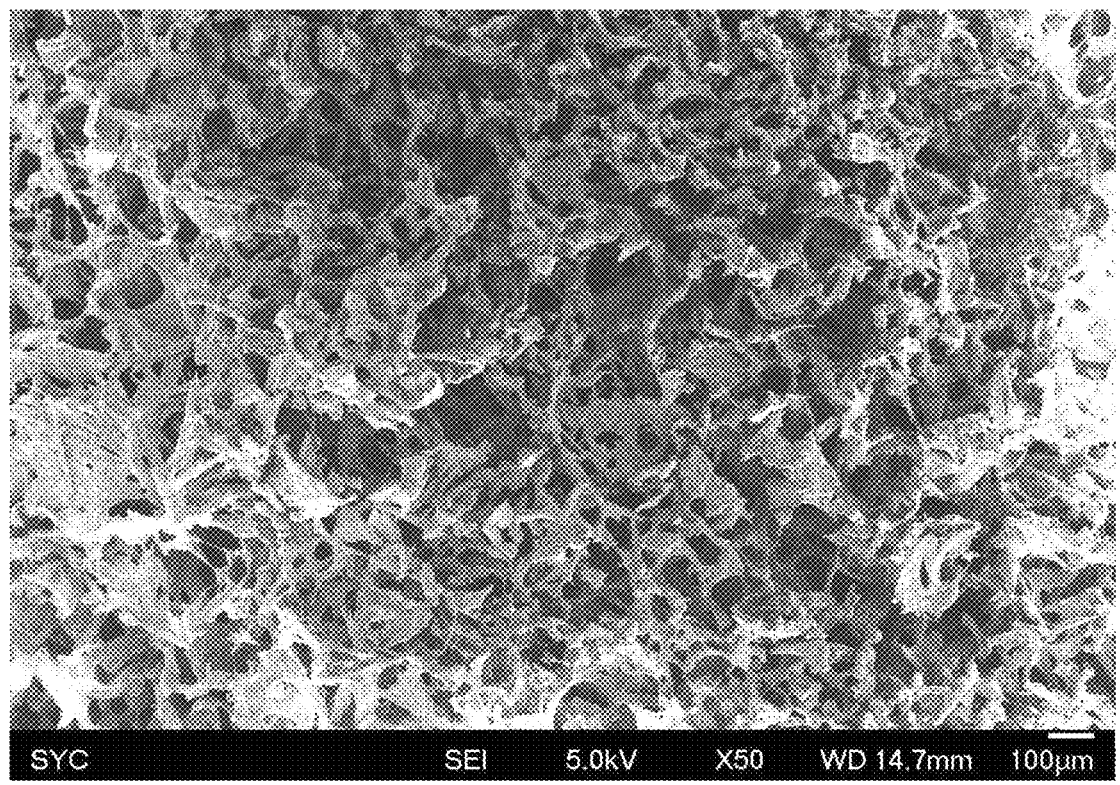

[Figure 5]
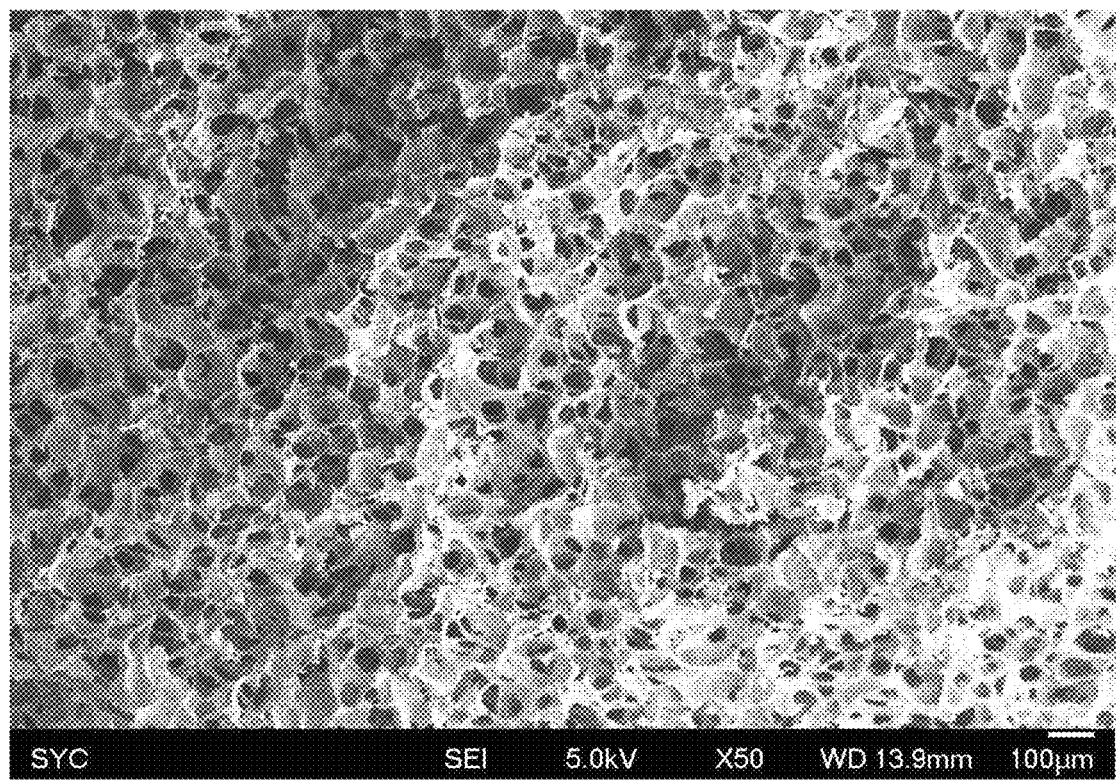

POLYMER NANOPARTICLE FREEZE-DRIED PRODUCT, AND PREPARATION METHOD THEREFOR

TECHNICAL FIELD

The present disclosure relates to easily reconstitutable lyophilized powder or cake of polymeric nanoparticle and a method for preparing the same, and more specifically, a lyophilized powder or cake of polymeric nanoparticle which is obtained by lyophilization process, including an annealing step, of an aqueous solution of polymeric nanoparticle comprising an amphiphilic block copolymer, a polylactic acid derivative having carboxyl terminal group and a lyophilization aid, and can be easily reconstituted within 5 minutes when reconstituted with a dilution solution for injection under atmospheric pressure; and a method for preparing the same.

BACKGROUND ART

Polymeric nanoparticle has been known as useful means for delivering drug specifically only to the target site of the patient. In particular, since the nanoparticle made up of biodegradable polymer is slowly degraded in body and disappears, it shows good biocompatibility and is actually applied to nano-drugs. However, such nanoparticle of biodegradable polymer is unstable in an aqueous solution, and thus it is usually formulated in freeze-dried form which requires reconstitution in use. At that time, because of the nature of polymer, it takes longer time to redisperse the polymeric nanoparticle in an injection medium, etc. as compared with other freeze-dried injection formulation, resulting in difficulty in actual use.

Various methods such as dialysis, emulsification, organic solvent evaporation, etc. are known for preparing polymeric nanoparticle. Korean Laid-open Patent Publication No. 10-2009-0049239 discloses a method for preparing polymeric micelle by adding dropwise methotrexate dissolved in organic solvent to an aqueous solution of a copolymer of methoxy polyethylene glycol and chitosan, dialyzing the mixture solution with distilled water, and lyophilizing it. In addition, US 2009/0036389 A1 discloses a method comprising dissolving an amphiphilic block copolymer and a hydrophobic drug in a solvent which is immiscible with water and has a boiling point lower than that of water (i.e., acetonitrile, methanol, ethanol and acetone), adding a sufficient amount of water thereto in a constant rate to form micelle and then adding a lyophilization aid thereto, and removing the organic solvent and lyophilizing it. Furthermore, Korean Patent No. 10-0421451 discloses a method for preparing a drug-containing polymer micelle composition comprising a) dissolving an amphiphilic block copolymer and a hydrophobic drug in an organic solvent, wherein the amphiphilic block copolymer consists of a hydrophilic block (A) and a hydrophobic block (B) having a terminal group substituted with a functional group for improving affinity with the hydrophobic drug, and evaporating the organic solvent to prepare a drug-polymer matrix; b) dissolving the drug-polymer matrix in water to prepare an aqueous solution of polymer micelle wherein the drug is encapsulated; and c) lyophilizing the aqueous solution of polymer micelle and then sterilizing it. Korean Patent No. 10-0531269 and U.S. Pat. No. 7,311,901 B2 disclose a method for preparing polymeric nanoparticle by dissolving an amphiphilic block copolymer, a monovalent metal salt of a polylactic acid derivative and a hydrophobic drug together in a volatile organic solvent to prepare a homogenous solution, removing the organic solvent by distillation under reduced pressure, and adding thereto water to prepare a micelle mixture, and adding thereto divalent metal cation. However, none of the above patent literatures mentions specific lyophilization method and reconstitution time after the lyophilization.

WO 2003/005992 A1 suggests a method for improving redissolution ability after lyophilization by adding one or more stabilizing agents selected from the group consisting of saccharide and polyethylene glycol, to drug-containing polymer micelle consisting of an amphiphilic block copolymer. However, this method has a problem of necessarily adding polyethylene glycol (an extra excipient) to saccharide (a conventional lyophilization agent). It will be preferable if the redissolution ability can be improved only through specifically controlling lyophilization conditions without using such an extra excipient.

In addition, US 2014/0199286 A1, Japanese Laid-open Patent Publication No. 2008-231067 A and Japanese Laid-open Patent Publication No. 2007-526329 A disclose the influence of lyophilization cycle to lyophilized formulation. However, US 2014/0199286 A1 is directed to a formulation consisting of protein, sodium phosphate, mannitol, trehalose and polysorbate; JP 2008-231067 A is directed to a formulation consisting of a quinolone-based antibiotic and a pH controlling agent only; and JP 2007-526329 A is directed to a formulation containing protein, nucleic acid or virus. As such, these literatures are not directed to a polymeric formulation using an amphiphilic block copolymer, etc. No method of improving lyophilization method of polymeric formulation has been disclosed so far.

CONTENTS OF THE INVENTION

Problems to be Solved

The purpose of the present invention is to provide a lyophilized powder or cake of polymeric nanoparticle which is a lyophilizate of biodegradable polymeric nanoparticle with good biocompatibility, and can be easily reconstituted within 5 minutes when reconstituted with a dilution solution for injection under atmospheric pressure, and a method for preparing the same.

Technical Means to Solve the Problems

One aspect of the present invention provides a method for preparing lyophilizate of polymeric nanoparticle by lyophilization process of a solution of polymeric nanoparticle, wherein the solution of polymeric nanoparticle comprises an amphiphilic block copolymer comprising a hydrophilic block (A) and a hydrophobic block (B) in A-B, A-B-A or B-A-B form; a polylactic acid derivative having carboxyl terminal group; and a lyophilization aid, wherein the solution of polymeric nanoparticle has a polymer concentration of 120 mg/ml of lower, wherein the lyophilization process comprises: a) a first freezing step where the solution of polymeric nanoparticle is frozen to a temperature in the range of −10 to −45° C.; b) an annealing step where the resulting product of the first freezing is heated to a temperature in the range of −25 to 0° C.; c) a second freezing step where the resulting product of the annealing is frozen to a temperature in the range of −10 to −45° C.; d) a primary drying step where the resulting product of the second freezing is dried at a temperature of lower than 0° C. under reduced pressure; and e) a secondary drying step where the resulting product of the primary drying is dried at a temperature of 0° C. or higher under reduced pressure; and wherein the lyophilizate of polymeric nanoparticle is reconstituted within 5 minutes when reconstituted with an aqueous solvent under atmospheric pressure.

According to a preferred aspect of the present invention, in the lyophilization process, the first freezing is conducted from an initial temperature of 0 to 25° C. to a final temperature of −10 to −45° C. with reducing the temperature for 0.5 to 24 hours followed by maintaining the temperature for 0.5 to 24 hours; the annealing is conducted from an initial temperature of −10 to −45° C. to a final temperature of −25 to 0° C. with elevating the temperature for 0.5 to 24 hours followed by maintaining the temperature for 0.2 to 8 hours; the second freezing is conducted from an initial temperature of −25 to 0° C. to a final temperature of −10 to −45° C. with reducing the temperature for 0.5 to 24 hours followed by maintaining the temperature for 1 to 24 hours; the primary drying is conducted under a vacuum degree of 50 to 500 mTorr at a temperature of −45 to below 0° C., for 24 to 96 hours; and the secondary drying is conducted under a vacuum degree of 50 to 500 mTorr at a temperature of 0 to 50° C., for 24 to 96 hours.

Another aspect of the present invention provides a lyophilizate of polymeric nanoparticle, comprising: an amphiphilic block copolymer comprising a hydrophilic block (A) and a hydrophobic block (B) in A-B, A-B-A or B-A-B form; a polylactic acid derivative having carboxyl terminal group; and a lyophilization aid, wherein the lyophilizate has a porosity of 70 to 99.9% and an average pore size of 70 μm or greater, and the lyophilizate is reconstituted within 5 minutes when reconstituted with an aqueous solvent under atmospheric pressure.

Still another aspect of the present invention provides a frozen polymeric nanoparticle, comprising: an amphiphilic block copolymer comprising a hydrophilic block (A) and a hydrophobic block (B) in A-B, A-B-A or B-A-B form; a polylactic acid derivative having carboxyl terminal group; and a lyophilization aid, wherein the frozen polymeric nanoparticle has a collapse temperature of −25° C. or higher.

Effects of the Invention

According to the present invention, a lyophilizate of biodegradable polymeric nanoparticle with good biocompatibility which can be easily reconstituted within 5 minutes, more preferably within 3 minutes, when reconstituted with a dilution solution for injection under atmospheric pressure, can be obtained, and therein a drug, especially a poorly water-soluble drug, can be contained suitably.

BRIEF EXPLANATION OF THE DRAWINGS

FIG. 1 is a graph showing the reconstitution time of Example 1 and Comparative Example 1 as measured in Experimental Example 1.

FIG. 2 is a graph showing the reconstitution time of Examples 1 and 2 and Comparative Example 2 as measured in Experimental Example 2.

FIG. 3 is a graph showing the reconstitution time of Example 1 in vacuo and under atmospheric pressure as measured in Experimental Example 3.

FIG. 4 is an electron micrograph of the lyophilizate obtained in Example 3.

FIG. 5 is an electron micrograph of the lyophilizate obtained in Comparative Example 1.

DETAILED DESCRIPTION TO CARRY OUT THE INVENTION

The present invention is explained in more detail below.

The solution of polymeric nanoparticle used in the present invention comprises an amphiphilic block copolymer comprising a hydrophilic block (A) and a hydrophobic block (B) in A-B, A-B-A or B-A-B form; a polylactic acid derivative having carboxyl terminal group; and a lyophilization aid, wherein the solution of polymeric nanoparticle has a polymer concentration of 120 mg/ml of lower (e.g., 1 mg/ml to 120 mg/ml), and more preferably 10 mg/ml to 100 mg/ml. If the solution of polymeric nanoparticle has a polymer concentration of higher than 120 mg/ml, there is a problem of increasing the reconstitution time of the lyophilizate. In terms of the reconstitution time, it is preferable that the polymer concentration is as low as possible. However, if the polymer concentration is too low, it is difficult to maintain the lyophilizate in cake form after the lyophilization, and thus the lyophilization aid should be added in a sufficient amount.

In an embodiment of the present invention, the amphiphilic block copolymer is a diblock copolymer wherein the hydrophilic block (A) and the hydrophobic block (B) are linked in A-B form, and the block copolymer is non-ionic. In addition, the amphiphilic block copolymer forms core-shell type polymeric micelle wherein the hydrophobic block (B) forms the core and the hydrophilic block (A) forms the shell.

The hydrophilic block (A) in the amphiphilic block copolymer is a water-soluble polymer. Concretely, it may be polyalkylene glycol such as polyethylene glycol, polyethylene-co-propylene glycol, etc.; polyalkylene glycol derivative such as monomethoxypolyalkylene glycol, monoacetoxypolyethylene glycol, etc.; polyvinyl alcohol; polyvinyl pyrrolidone; or polyacrylamide, etc.; and more concretely, it may be selected from the group consisting of polyethylene glycol, monomethoxypolyethylene glycol, polyvinyl pyrrolidone, polyvinyl alcohol and polyacrylamide. Preferably, the hydrophilic block (A) has a number average molecular weight of 500 to 50,000 Daltons, more concretely 500 to 20,000 Daltons, and still more concretely 1,000 to 20,000 Daltons.

The hydrophobic block (B) in the amphiphilic block copolymer is a water-insoluble polymer with good biocompatibility and biodegradability. Concretely, it may be polyester, polyanhydride, polyamino acid, polyorthoester or polyphosphazine, etc.; and more concretely, it may be selected from the group consisting of polylactide, polyglycolide, polydioxan-2-one, polycaprolactone, polylactic-co-glycolide, polylactic-co-caprolactone, polylactic-co-dioxan-2-one and polyglycolic-co-caprolactone, and derivatives thereof where the terminal carboxylic acid is substituted with fatty acid group. In addition, the fatty acid group, which can be a substituent to the terminal carboxylic acid, may be butyric acid group, propionic acid group, acetic acid group, stearic acid group or palmitic acid group. Preferably, the hydrophobic block (B) has a number average molecular weight of 500 to 50,000 Daltons, more concretely 500 to 20,000 Daltons, and still more concretely 1,000 to 20,000 Daltons.

According to an embodiment of the present invention, in order to form stable polymeric micelle in an aqueous solution phase, the weight ratio of the hydrophilic block (A) and the hydrophobic block (B) (the ratio of the hydrophilic block (A): the hydrophobic block (B)) in the amphiphilic block copolymer is 2:8 to 8:2, more concretely 3:7 to 7:3, and still more concretely 4:6 to 6:4. If the ratio of the hydrophilic block (A) is too low, the polymer may not form polymeric micelle in an aqueous solution. If the ratio of the hydrophilic block (A) is too high, the hydrophilicity may increase excessively, and thus the stability may deteriorate.

In an embodiment of the present invention, the polylactic acid derivative having carboxyl terminal group may be one having a group with alkali metal ion bonded to the terminal carboxylic acid group or carboxyl group, for example, one or more selected from the group consisting of polylactic acid, polylactide, polyglycolide, polymandelic acid, polycaprolactone, polydioxan-2-one, polyamino acid, polyorthoester, polyanhydride and copolymers thereof; and more concretely, the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone, and copolymer of D,L-lactic acid and 1,4-dioxan-2-one.

In an embodiment of the present invention, the alkali metal ion may be a monovalent metal ion of sodium, potassium or lithium.

In the polylactic acid derivative, the other terminal group, which is not the carboxyl terminal group, may be one or more selected from the group consisting of hydroxy, methoxy, ethoxy, acetoxy, benzoyloxy, decanoyloxy and palmitoyloxy.

In the polylactic acid derivative, the carboxyl terminal group having alkali metal ion bonded thereto acts as a hydrophilic group in an aqueous solution with pH of 4 or higher, and forms polymeric micelle in the aqueous solution. Also, the polylactic acid salt or its derivative exists in solid state at room temperature, and even if it is exposed to moisture in the air, it takes very stable form because its pH is neutral.

The polylactic acid derivative having carboxyl terminal group with alkali metal ion bonded thereto plays a role of improving the encapsulation efficiency of drug by being added to the micelle consisting of the amphiphilic block copolymer and hardening the inside of the core of the micelle. The polylactic acid derivative is dissolved in an aqueous solution and forms micelle through the balance of the hydrophilic part and the hydrophobic part existing in the polylactic acid derivative molecule. Thus, if the molecular weight of the hydrophobic ester part becomes too high, the association of the terminal carboxyl anions showing hydrophilicity becomes difficult and the micelle cannot be formed well, and if the molecular weight is too low, the polymer is dissolved in water completely and the micelle formation itself is difficult. In an embodiment, the preferable number average molecular weight of polylactic acid derivative which can form micelle in pH of 4 or higher is 500 to 5,000 Daltons, and more concretely 500 to 2,500 Daltons. If the molecular weight is too low, it is dissolved in water completely and the micelle formation itself is difficult. If the molecular weight is too high, the hydrophobicity increases too high and even the dissolution in aqueous solution is difficult, and accordingly the micelle cannot be formed. Such a molecular weight of the polylactic acid derivative can be achieved by properly controlling the reaction temperature, time, etc. in its preparation.

In an embodiment, the polylactic acid derivative having carboxyl terminal group with alkali metal ion bonded thereto can be represented by the following formula 1.

[Formula 1]

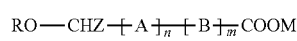

(In formula 1,
A is

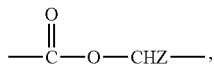

where Z is hydrogen, methyl group or phenyl group;
B is

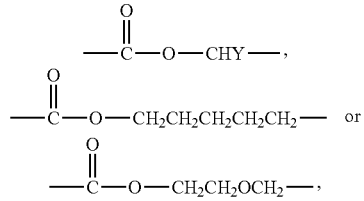

where Y is hydrogen, methyl group or phenyl group;
R is hydrogen, acetyl group, benzoyl group, decanoyl group, palmitoyl group, methyl group or ethyl group;
M is sodium, potassium or lithium;
n is an integer of 1 to 30; and
m is an integer of 0 to 20.)

More concretely, the polylactic acid salt or derivative thereof having carboxyl terminal group with alkali metal ion bonded thereto can be represented by the following formula 2.

[Formula 2]

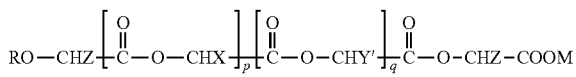

(In formula 2,
Z, R and M are the same as defined in formula 1;
X is methyl group;
Y' is hydrogen or phenyl group;
p is an integer of 0 to 25; and
q is an integer of 0 to 25,
provided that p+q is an integer of 5 to 25.)

In another embodiment, the polylactic acid derivative having carboxyl terminal group with alkali metal ion bonded thereto can be represented by the following formula 3 or 4.

[Formula 3]

(In formula 3,
W-M is

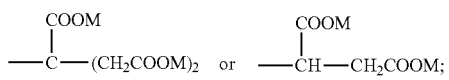

and
PLA is D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone, or copolymer of D,L-lactic acid and 1,4-dioxan-2-one.)

[Formula 4]

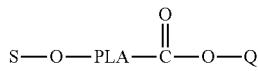

(In formula 4,
S is

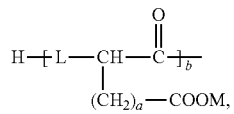

where L is —$NR_1$— or —O— (wherein $R_1$ is hydrogen or $C_1$~$C_{10}$ alkyl), a is an integer of 0 to 4, b is an integer of 1 to 10, and M is sodium, potassium or lithium;

Q is $CH_3$, $CH_2CH_3$, $CH_2CH_2CH_3$, $CH_2CH_2CH_2CH_3$ or $CH_2C_6H_5$; and PLA is D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone, or copolymer of D,L-lactic acid and 1,4-dioxan-2-one.)

The amphiphilic block copolymer and the polylactic acid derivative having carboxyl terminal group together in water may form an aqueous solution of mixed micelle.

In an embodiment, the solution of polymeric nanoparticle may further comprise poorly water-soluble drug, and as a result, the poorly water-soluble drug can be contained within the mixed micelle. The method for containing the poorly water-soluble drug within the mixed micelle is, for example, as follows: dissolving the poorly water-soluble drug, the amphiphilic block copolymer and the polylactic acid derivative having carboxyl terminal group in an organic solvent, removing the organic solvent, and adding thereto water to prepare mixed micelle; or dissolving the poorly water-soluble drug and the polylactic acid derivative having carboxyl terminal group in an organic solvent, removing the organic solvent, and adding to the dried product an aqueous solution where the amphiphilic block copolymer is dissolved in water, to prepare mixed micelle.

In an embodiment, the organic solvent may be one or more selected from the group consisting of alcohol, dichloromethane, chloroform, acetone, tetrahydrofuran, acetic acid, acetonitrile and dioxane. In an embodiment, the amount of the organic solvent may be 0.5 to 30% by weight, concretely 0.5 to 15% by weight, and more concretely 1 to 10% by weight, based on the total weight of the composition. If the amount of the organic solvent is less than 0.5% by weight, it is difficult to dissolve the drug. If the amount of the organic solvent is greater than 30% by weight, the drug may precipitate during the reconstitution. The poorly water-soluble drug and the polymer may be dissolved in the organic solvent at the same time or sequentially. The drug and the polymer may be added to the organic solvent at the same time and dissolved, or the polymer may be dissolved first and the drug may be dissolved therein, or the drug may be dissolved in the organic solvent first and the polymer may be added thereto. The temperature for dissolving the poorly water-soluble drug in the organic solvent may be 0 to 60° C., more concretely 10 to 50° C., and still more concretely 10 to 40° C. for preventing decomposition of the drug, but it is not limited thereto. The removal of the organic solvent may be conducted by distillation under reduced pressure, pneumatic conveying drying, heat drying, etc. Also, when the organic solvent is used in a small amount, the step for removing the organic solvent may be omitted. The aqueous solution may be water, distilled water, distilled water for injection, physiological saline, 5% glucose, buffer, etc. The step for preparing micelle is conducted by adding the aqueous solution at a temperature of 0 to 80° C., more concretely 10 to 60° C., and still more concretely 10 to 40° C., to form polymeric micelle.

The poorly water-soluble drug may be selected from ones having solubility in water (25° C.) of 100 mg/mL or less. Also, it may be selected from antineoplastic agents, antifungal agents, immunosuppressants, analgesics, anti-inflammatory agents, antiviral agents, anxiolytic sedatives, contrasting agents, corticosteroids, diagnostic agents, diagnostic imaging agents, diuretics, prostaglandins, radio-pharmaceuticals, sex hormones including steroid, and combinations thereof, but it is not limited thereto.

In an embodiment, the poorly water-soluble drug may be selected from antineoplastic agents, and concretely it may be a taxane anticancer agent. For example, the taxane anticancer agent may be one or a mixture of two or more selected from the group consisting of paclitaxel, docetaxel, carbazitaxel, 7-epipaclitaxel, t-acetyl paclitaxel, 10-desacetyl-paclitaxel, 10-desacetyl-7-epipaclitaxel, 7-xylosylpaclitaxel, 10-desacetyl-7-glutarylpaclitaxel, 7-N,N-dimethylglycylpaclitaxel and 7-L-alanyl paclitaxel. More concretely, it is paclitaxel or docetaxel.

In another embodiment, the poorly water-soluble drug may be selected from antifungal agents, and concretely it may be an azole antifungal agent. For example, the azole antifungal agent may be one or a mixture of two or more selected from the group consisting of voriconazole, posaconazole, ravuconazole, fluconazole, econazol, ketoconazole and itraconazole. More concretely, it is voriconazole.

In an embodiment, based on the total weight of the amphiphilic block copolymer and the polylactic acid derivative having carboxyl terminal group, 0.1 to 99.9% by weight of the amphiphilic block copolymer and 0.1 to 99.9% by weight of the polylactic acid derivative may be used; preferably 20 to 95% by weight of the amphiphilic block copolymer and 5 to 80% by weight of the polylactic acid derivative may be used; and more preferably 50 to 90% by weight of the amphiphilic block copolymer and 10 to 50% by weight of the polylactic acid derivative may be used. In another embodiment, based on the total weight of the amphiphilic block copolymer, the polylactic acid derivative having carboxyl terminal group and the poorly water-soluble drug, 0.1 to 20% by weight of the poorly water-soluble drug may be used.

In an embodiment, the solution of polymeric nanoparticle may further comprise salt of divalent or trivalent metal ion, and as a result, the salt of divalent or trivalent metal ion may be added to the aqueous solution of mixed micelle. Such divalent or trivalent metal ion is added to further improve the stability of the polymeric micelle formed by mixing the amphiphilic block copolymer and the polylactic acid derivative having carboxyl terminal group. The divalent or trivalent metal ion is bonded to the carboxyl terminal group of the polylactic acid derivative and polymeric micelle having bonded divalent or trivalent metal ion is formed. For example, in a polylactic acid salt or its derivative having monovalent alkali metal ion bonded to the carboxyl terminal group thereof, the divalent or trivalent metal ion is substituted for the monovalent alkali metal cation bonded to the carboxyl terminal group to form an ionic bond, and this ionic bond plays a role of further improving the stability of the polymeric micelle due to the strong ionic strength.

In an embodiment, the divalent or trivalent metal ion may be selected from the group consisting of calcium ($Ca^{2+}$), magnesium ($Mg^{2+}$), barium ($Ba^{2+}$), chromium ($Cr^{3+}$), iron ($Fe^{3+}$), manganese ($Mn^{2+}$), nickel ($Ni^{2+}$), copper ($Cu^{2+}$), zinc ($Zn^{2+}$) and aluminum ($Al^{3+}$). In another embodiment, the divalent or trivalent metal ion is added to the mixed polymer composition of the amphiphilic block copolymer and the polylactic acid derivative in form of sulfate salt, chloride salt, carbonate salt, phosphate salt or hydroxide. Concretely, it is added in form of calcium chloride ($CaCl_2$), magnesium chloride ($MgCl_2$), zinc chloride ($ZnCl_2$), aluminum chloride ($AlCl_3$), ferric chloride ($FeCl_3$), calcium carbonate ($CaCO_3$), magnesium carbonate ($MgCO_3$), calcium phosphate ($Ca_3(PO_4)_2$), magnesium phosphate ($Mg_3(PO_4)_2$), aluminum phosphate ($AlPO_4$), magnesium sulfate ($MgSO_4$), calcium hydroxide ($Ca(OH)_2$), magnesium hydroxide ($Mg(OH)_2$), aluminum hydroxide ($Al(OH)_3$) or zinc hydroxide ($Zn(OH)_2$). Also, the divalent or trivalent metal ion may be added in amount of 0.001 to 10 equivalents, and more concretely 0.5 to 2.0 equivalents, to the equivalent of the carboxyl terminal group of the polylactic acid derivative.

In an embodiment, the lyophilization aid (also referred to as "lyophilizing agent") may be selected from the group consisting of sugar, sugar alcohol, and mixtures thereof. The sugar may be one or more selected from the group consisting of lactose, maltose, sucrose and trehalose, and the sugar alcohol may be one or more selected from the group consisting of mannitol, sorbitol, maltitol, xylitol and lactitol. The lyophilization aid is added so that the lyophilized composition may maintain cake form. In addition, after the lyophilization of the polymeric nanoparticle composition, the lyophilization aid plays a role of helping uniform dissolution of the lyophilizate in short time in the course of reconstitution. In an embodiment, the amount of the lyophilization aid is 1 to 90% by weight, and more concretely 10 to 60% by weight, based on the total dry weight of the lyophilized composition.

In an embodiment, the polymer concentration in the original solution of polymeric nanoparticle to be lyophilized (i.e., the concentration of polymer comprising the amphiphilic block copolymer and the polylactic acid derivative having carboxyl terminal group) is 1 mg/ml or higher, and more preferably 10 mg/ml or higher; and 120 mg/ml or lower, more preferably 100 mg/ml or lower, and still more preferably 50 mg/ml or lower. If the polymer concentration in the solution is too high, polymer is likely to aggregate during reconstitution after the lyophilization, by which it takes too long time for complete dissolution. If the polymer concentration is too low, the volume of solution in use becomes too large, which makes the solution inconvenient for use.

The lyophilization process comprises:
a) a first freezing step where the solution of polymeric nanoparticle is frozen to a temperature in the range of −10 to −45° C.;
b) an annealing step where the resulting product of the first freezing is heated to a temperature in the range of −25 to 0° C.;
c) a second freezing step where the resulting product of the annealing is frozen to a temperature in the range of −10 to −45° C.;
d) a primary drying step where the resulting product of the second freezing is dried at a temperature of lower than 0° C. under reduced pressure; and
e) a secondary drying step where the resulting product of the primary drying is dried at a temperature of 0° C. or higher under reduced pressure.

Through the lyophilization process as mentioned above, the ice crystal becomes large and as a result, the pore of the lyophilized cake becomes large, thereby making permeation of water easy during reconstitution and thus reducing the reconstitution time.

More concretely, in the lyophilization process,
the first freezing is conducted from an initial temperature of 0 to 35° C. (more preferably 0 to 25° C., and most preferably 0 to 15° C.) to a final temperature of −10 to −45° C. (more preferably −20 to −40° C., and most preferably −30 to −40° C.) with reducing the temperature for 0.5 to 24 hours (more preferably 0.5 to 12 hours, and most preferably 0.5 to 6 hours), followed by maintaining the temperature for 0.5 to 24 hours (more preferably 0.5 to 12 hours, and most preferably 0.5 to 6 hours);

the annealing is conducted from an initial temperature of −10 to −45° C. (more preferably −20 to −40° C., and most preferably −30 to −40° C.), to a final temperature of −25 to 0° C. (more preferably −25 to −10° C., and most preferably −25 to −15° C.) with elevating the temperature for 0.5 to 24 hours (more preferably 0.5 to 12 hours, and most preferably 0.5 to 6 hours), followed by maintaining the temperature for 0.2 to 12 hours (more preferably 0.5 to 8 hours, and most preferably 0.5 to 4 hours);

the second freezing is conducted from an initial temperature of −25 to 0° C. (more preferably −25 to −10° C., and most preferably −25 to −15° C.) to a final temperature of −10 to −45° C. (more preferably −20 to −40° C., and most preferably −30 to −40° C.) with reducing the temperature for 0.5 to 24 hours (more preferably 0.5 to 12 hours, and most preferably 0.5 to 6 hours), followed by maintaining the temperature for 0.5 to 24 hours (more preferably 0.5 to 12 hours, and most preferably 0.5 to 6 hours);

the primary drying is conducted under a vacuum degree of 50 to 500 mTorr (more preferably 50 to 150 mTorr, and most preferably 50 to 100 mTorr) at a temperature of −45 to below 0° C. (more preferably −5 to −40° C., and most preferably −10 to −30° C.) for 24 to 96 hours (more preferably 24 to 72 hours, and most preferably 48 to 72 hours); and the secondary drying is conducted under a vacuum degree of 50 to 500 mTorr (more preferably 50 to 150 mTorr, and most preferably 50 to 100 mTorr) at a temperature of 0 to 50° C. (more preferably 5 to 40° C., and most preferably 15 to 35° C.) for 6 to 48 hours (more preferably 6 to 24 hours, and most preferably 12 to 24 hours).

In an embodiment, the primary drying step may comprise: maintaining the temperature at −45~below −20° C. for 1 to 5 hours; elevating the temperature from −45~below −20° C. to −20~below −10° C. for 2 to 6 hours; maintaining the temperature at −20~below −10° C. for 10 to 40 hours; elevating the temperature from −20~below −10° C. to −10~below 0° C. for 1 to 5 hours; and maintaining the temperature at −10~below 0° C. for 10 to 40 hours.

In an embodiment, the secondary drying step may comprise: elevating the temperature from −10~below 0° C. to 0~20° C. for 0.5 to 3 hours; maintaining the temperature at 0~below 20° C. for 0.5 to 6 hours; elevating the temperature from 0~below 20° C. to 20~50° C. for 2 to 9 hours; and maintaining the temperature at 20~50° C. for 3 to 30 hours.

The method for preparing lyophilizate of polymeric nanoparticle of the present invention may further comprise a step of introducing the resulting product of the above-explained lyophilization process into a vial, and filling the vial with nitrogen gas and sealing it, or sealing the vial in vacuo.

In an embodiment, the lyophilizate of polymeric nanoparticle as prepared above comprises: 0.1 to 78.9% by weight of amphiphilic block copolymer; 20.0 to 98.8% by weight of polylactic acid derivative having carboxyl terminal group bonded to divalent or trivalent metal ion; 0.1 to 20.0% by weight of poorly water-soluble drug; and 1 to 79.8% by weight of lyophilization aid.

The lyophilizate of polymeric nanoparticle prepared by the method of the present invention is characterized in that it is reconstituted within 5 minutes, and more preferably within 3 minutes, when reconstituted with an aqueous solvent under atmospheric pressure.

In addition, another aspect of the present invention provides a lyophilizate of polymeric nanoparticle, comprising: an amphiphilic block copolymer comprising a hydrophilic block (A) and a hydrophobic block (B) in A-B, A-B-A or B-A-B form; a polylactic acid derivative having carboxyl terminal group; and a lyophilization aid, wherein the lyophilizate has a porosity of 70 to 99.9% and an average pore size of 70 μm or greater (for example, 70 to 200 μm), more preferably 90 μm or greater (for example, 90 to 200 μm), and still more preferably 100 μm or greater (for example, 100 to 200 μm), and the lyophilizate is reconstituted within 5 minutes, and more preferably within 3 minutes, when reconstituted with an aqueous solvent under atmospheric pressure. If the porosity is too low or the pore size is too small, permeation of aqueous solution during reconstitution is delayed and thus the reconstitution time increases.

In an embodiment, the porosity n (%) may be calculated according to the following mathematical formula 1.

$$n = (V - Vs)/V \times 100 (\%) \quad \text{[Mathematical formula 1]}$$

wherein Vs is the volume of the solid part only (Volume of the lyophilized cake−Volume of water), and V is the total volume including pore (Volume of the lyophilized cake).

Still another aspect of the present invention provides a frozen polymeric nanoparticle, comprising: an amphiphilic block copolymer comprising a hydrophilic block (A) and a hydrophobic block (B) in A-B, A-B-A or B-A-B form; a polylactic acid derivative having carboxyl terminal group; and a lyophilization aid, wherein the frozen polymeric nanoparticle has a collapse temperature of preferably −25 to −5° C., more preferably −20 to −5° C., and most preferably −15 to −5° C.

The collapse temperature refers to the maximum temperature which is allowable during the primary drying step, and means that if the primary drying is conducted at a temperature higher than this temperature, the shape of the cake is distorted or collapsed. The collapse temperature is measured by using a freeze-drying microscope.

As the collapse temperature is higher, the lyophilization time can be shortened because the primary drying can be conducted at a higher temperature without affecting the shape of the lyophilized cake.

The present invention is explained in more detail by the following examples. However, these examples seek to illustrate the present invention only, and the scope of the present invention is not limited by the examples in any manner.

EXAMPLES

The amphiphilic block copolymer and the polylactic acid salt or derivative thereof having carboxyl terminal group with alkali metal ion bonded thereto used in the following examples were prepared according to the method disclosed in WO 03/033592 A1, the disclosure of which is herein incorporated by reference in its entirety.

Examples 1 and 2, and Comparative Example 2: Preparation of Lyophilized Cake of Polymeric Nanoparticle As an amphiphilic block copolymer, monomethoxypolyethylene glycol-polylactide having a number average molecular weight of 2,000 to 1,766 Daltons was synthesized. Also, D,L-PLA-COONa having a number average molecular weight of 1,800 Daltons was synthesized.

With the amounts shown in the following Table 1, 3.0 mL of dichloromethane was added to the polylactic acid salt and stirred at 40° C. until the solution became transparent. By using a rotary evaporator connected to a vacuum pump, dichloromethane was removed by evaporation under reduced pressure for about 3 hours to generate white foam solid. Separately, water of 60° C. was added to the amphiphilic block copolymer and stirred until the polymer lump was completely dissolved, and then the solution was cooled to room temperature. The amphiphilic block copolymer solution of room temperature was added to the white foam solid, and with maintaining the temperature at about 35° C., the micellization was conducted until the solution became transparent in blue. Calcium chloride was thereto added to form polymeric nanoparticle. To the polymeric nanoparticle solution, D-mannitol as a lyophilizing agent was added and dissolved completely, and then the solution was filtered using a filter with a pore size of 200 nm, and lyophilized according to the following lyophilization conditions to prepare the lyophilized cake of polymeric nanoparticle.

TABLE 1

| | Amount (mg) | | | | |
|---|---|---|---|---|---|
| | Polylactic acid salt[1] | Amphiphilic block copolymer[2] | Metal ion salt[3] | Lyophilizing agent[4] | Water (mL) |
| Example 1 | 1,320.0 | 2,640.0 | 108.0 | 720.0 | 36 |
| Example 2 | 1,320.0 | 2,640.0 | 108.0 | 720.0 | 29 |
| Comparative Example 2 | 1,320.0 | 2,640.0 | 108.0 | 720.0 | 22 |

[1] D,L-PLA-COONa: Number average molecular weight of 1,800 Daltons
[2] Monomethoxypolyethylene glycol-polylactide: Number average molecular weight of 2,000 to 1,766 Daltons
[3] Calcium chloride dihydrate
[4] D-mannitol

TABLE 2

| | Conditions for preparing lyophilizate | |
|---|---|---|
| | Polymer concentration in the original solution to be lyophilized[1] | Lyophilization conditions[2] |
| Example 1 | 99.0 | Including annealing process |
| Example 2 | 118.8 | Including annealing process |
| Comparative Example 2 | 148.5 | Including annealing step |

[1] Concentration of the sum of the polylactic acid salt and the amphiphilic block copolymer (mg/ml)
[2] Conditions for freezing and drying provided in Table 3

TABLE 3

|  | Temperature (° C.) | Time (min) | Vacuum degree (mTorr) | Temperature setting |
|---|---|---|---|---|
| <Freezing conditions> | | | | |
| Step 1 | 5 | 30 | Atmospheric pressure | Maintained |
| Step 2 | −40 | 90 | Atmospheric pressure | Reduced |
| Step 3 | −40 | 120 | Atmospheric pressure | Maintained |
| Step 4 | −15 | 100 | Atmospheric pressure | Elevated |
| Step 5 | −15 | 120 | Atmospheric pressure | Maintained |
| Step 6 | −40 | 80 | Atmospheric pressure | Reduced |
| Step 7 | −40 | 120 | Atmospheric pressure | Maintained |
| <Primary drying conditions> | | | | |
| Step 1 | −40 | 180 | 100 | Maintained |
| Step 2 | −15 | 250 | 100 | Elevated |
| Step 3 | −15 | 2,160 | 100 | Maintained |
| Step 4 | −5 | 100 | 100 | Elevated |
| Step 5 | −5 | 1,630 | 100 | Maintained |
| <Secondary drying conditions> | | | | |
| Step 1 | 5 | 100 | 50 | Elevated |
| Step 2 | 5 | 200 | 50 | Maintained |
| Step 3 | 25 | 400 | 50 | Elevated |
| Step 4 | 25 | 740 | 50 | Maintained |

Comparative Example 1: Preparation of Lyophilized Cake of Polymeric Nanoparticle without Annealing Step The preparation was carried out in the same method as that of Example 1, excepting that the annealing step and the second freezing step were not conducted. That is, the lyophilization conditions of the following Table 4 were used.

TABLE 4

|  | Temperature (° C.) | Time (min) | Vacuum degree (mTorr) | Temperature setting |
|---|---|---|---|---|
| <Freezing conditions> | | | | |
| Step 1 | 5 | 30 | Atmospheric pressure | Maintained |
| Step 2 | −40 | 90 | Atmospheric pressure | Reduced |
| Step 3 | −40 | 120 | Atmospheric pressure | Maintained |

Experimental Example 1: Effect of Lyophilization Condition on the Reconstitution Time of Polymeric Nanoparticle Cake Each of the lyophilized cakes of polymeric nanoparticle prepared in Example 1 and Comparative Example 1 was reconstituted according to the following method, measuring the reconstitution time.

Reconstitution Method 36 mL of distilled water for injection at about 20° C. was added to a vial containing 4,788 mg of the lyophilized cake, and the vial was vigorously shaken by hand for 1 minute and then softly shaken by hand until all solid components therein were dissolved. The reconstitution time was checked. The measured results are shown in FIG. 1.

As can be seen from the measured results of reconstitution time of FIG. 1, the case with the lyophilization conditions of, after the first freezing, conducting the annealing step of elevating the temperature in the range of below or equal to the melting point and maintaining the temperature for a constant time, and then conducting the second freezing (Example 1: 3.7 minutes) showed the reconstitution time significantly shorter than the case of simple freezing with directly reducing the temperature (Comparative Example 1: 5.9 minutes).

Experimental Example 2: Effect of Concentration in the Original Solution for Lyophilization on the Reconstitution Time of Polymeric Nanoparticle Cake Each of the lyophilized cakes of polymeric nanoparticle prepared in Examples 1 and 2 and Comparative Example 2 was reconstituted according to the same method as that of Experimental Example 1, measuring the reconstitution time. The measured results are shown in FIG. 2.

As can be seen from the measured results of reconstitution time of FIG. 2, there is a tendency that the reconstitution time became longer if the concentration in the original solution used in the lyophilization became higher. In particular, if the concentration was greater than 1.2 mg/mL (about 120 mg/mL as polymer concentration), the reconstitution time was increased drastically.

Experimental Example 3: Effect of Vacuum Degree in Vial During Reconstitution on the Reconstitution Time of Polymeric Nanoparticle Cake The lyophilized cake of polymeric nanoparticle prepared in Example 1 was reconstituted according to the same method as that of Experimental Example 1, measuring the reconstitution time with varying the vacuum degree (vacuum state vs. atmospheric pressure) in the vial during the reconstitution. The measured results are shown in FIG. 3.

As can be seen from the measured results of reconstitution time of FIG. 3, when water was added while the inside of the vial was maintained in vacuo during the reconstitution, the reconstitution time was increased significantly and the deviation of the reconstitution time between vials was very large.

Experimental Example 4: Effect of Freezing Condition on the Collapse Temperature of the Original Solution of Polymeric Nanoparticle for Lyophilization The original solution of polymeric nanoparticle for lyophilization with the composition of Example 1 was frozen under the freezing conditions of the following Table 5, and the collapse temperature of the obtained frozen product was measured by using Freeze Drying Microscope.

TABLE 5

<Freezing conditions and collapse temperature>

| Freezing method | | Temperature (° C.) | Cooling speed (° C./min) | Annealing condition | | Heating speed (° C./min) | Collapse temperature (° C.) |
|---|---|---|---|---|---|---|---|
| | | | | Temperature (° C.) | Retention time (min) | | |
| Simple freezing | Fast | −45 | −20 | NA | NA | NA | −30.3 |
| | Slow | −45 | −2 | NA | NA | NA | −25.7 |
| First freezing-annealing-second freezing[1] | | −45 | −20 | −15 | 10 | 2 | −21.3 |

[1])Cooling at a speed of −20° C./min to −45° C. (first freezing); then heating at a speed of 2° C./min to −15° C. and maintaining at −15° C. for 10 minutes (annealing); and then cooling at a speed of −20° C./min to −45° C. (second freezing)
NA: Not applicable As can be seen from the results of Table 5, for the original solution of polymeric nanoparticle for lyophilization with the composition of Example 1, the collapse temperature of the freezing process including the annealing was higher than those of the simple freezing processes without annealing. Accordingly, it is confirmed that if annealing is conducted during the freezing, the lyophilization can be done more efficiently.

Example 3: Preparation of Lyophilized Cake of Polymeric Nanoparticle Containing Docetaxel The preparation was carried out in the same method as that of Example 1, except that 3.0 mL of dichloromethane was added to docetaxel of the amount shown in the following Table 6 and the polylactic acid salt and stirred at 40° C. until the solution became transparent.

TABLE 6

| | Amount (mg) | | | | | |
|---|---|---|---|---|---|---|
| | Docetaxel | Polylactic acid salt [1] | Amphiphilic block copolymer [2] | Metal ion salt[3] | Lyophilizing agent [4] | Water (mL) |
| Example 3 | 40.0 | 1,320.0 | 2,640.0 | 108.0 | 720.0 | 36.0 |

[1]) D,L-PLA-COONa: Number average molecular weight of 1,800 Daltons
[2]) Monomethoxypolyethylene glycol-polylactide: Number average molecular weight of 2,000 to 1,766 Daltons
[3])Calcium chloride dihydrate
[4]) D-mannitol 36 mL of distilled water for injection at about 20° C. was added to a vial containing 4,828 mg of the lyophilized cake of polymeric nanoparticle containing docetaxel as prepared above, and the vial was vigorously shaken by hand for 1 minute and then softly shaken by hand until all solid components therein were dissolved. The reconstitution time taken until all solid components in the vial were dissolved was 4.2 minutes.

In addition, the lyophilizate of polymeric nanoparticle containing docetaxel as prepared above (docetaxel-PNP) showed porosity of 90.0% (1.0 mg/mL as docetaxel concentration in the original solution for lyophilization).

The lyophilizate of Example 3 was observed with 50 times magnification by an electron microscope, and the result is shown in FIG. 4. As shown in FIG. 4, it can be known that the lyophilizate according to the present invention has amorphous large pores. For comparison, the lyophilizate obtained in Comparative Example 1 was observed with 50 times magnification by an electron microscope, and the result is shown in FIG. 5. As can be seen from FIG. 4, FIG. 5 and Table 7, it is confirmed that the lyophilizate obtained according to the present invention has larger pores as compared with the lyophilizate obtained according to the conventional method.

TABLE 7

| | Pore size (µm) | |
|---|---|---|
| | Average short diameter | Average long diameter |
| Example 3 | 72.3 | 103.8 |
| Comparative Example 1 | 62.3 | 68.2 |

Example 4: Preparation of Lyophilized Cake of Polymeric Nanoparticle Containing Paclitaxel The preparation was carried out in the same method as that of Example 1, except that 3.0 mL of dichloromethane was added to paclitaxel of the amount shown in the following Table 8 and the polylactic acid salt and stirred at 45° C. until the solution became transparent.

TABLE 8

| | Amount (mg) | | | | | |
|---|---|---|---|---|---|---|
| | Paclitaxel | Polylactic acid salt [1] | Amphiphilic block copolymer [2] | Metal ion salt [3] | Lyophilizing agent [4] | Water (mL) |
| Example 4 | 30.0 | 570.0 | 2,400.0 | 64.5 | 510.0 | 26.4 |

[1] D,L-PLA-COONa: Number average molecular weight of 1,800 Daltons
[2] Monomethoxypolyethylene glycol-polylactide: Number average molecular weight of 2,000 to 1,766 Daltons
[3] Calcium chloride dihydrate
[4] D-mannitol 26.4 mL of distilled water for injection at about 25° C. was added to a vial containing 3,574.5 mg of the lyophilized cake of polymeric nanoparticle containing paclitaxel as prepared above, and the vial was vigorously shaken by hand for 1 minute and then softly shaken by hand until all solid components therein were dissolved. The reconstitution time taken until all solid components in the vial were dissolved was 1.6 minutes.

Example 5: Preparation of Lyophilized Cake of Polymeric Nanoparticle Containing Voriconazole The preparation was carried out in the same method as that of Example 1, excepting that 3.0 mL of dichloromethane was added to voriconazole of the amount shown in the following Table 9 and the polylactic acid salt and stirred at 40° C. until the solution became transparent.

TABLE 9

| | Amount (mg) | | | | | |
|---|---|---|---|---|---|---|
| | Voriconazole | Polylactic acid salt [1] | Amphiphilic block copolymer [2] | Metal ion salt [3] | Lyophilizing agent [4] | Water (mL) |
| Example 5 | 200.0 | 885.0 | 1,770.0 | 72.0 | 483.0 | 36.0 |

[1] D,L-PLA-COONa: Number average molecular weight of 1,800 Daltons
[2] Monomethoxypolyethylene glycol-polylactide: Number average molecular weight of 2,000 to 1,766 Daltons
[3] Calcium chloride dihydrate
[4] D-mannitol 36.0 mL of distilled water for injection at about 25° C. was added to a vial containing 3,410 mg of the lyophilized cake of polymeric nanoparticle containing voriconazole as prepared above, and the vial was vigorously shaken by hand for 1 minute and then softly shaken by hand until all solid components therein were dissolved. The reconstitution time taken until all solid components in the vial were dissolved was 2.9 minutes.

The invention claimed is:

1. A method for preparing lyophilizate of polymeric nanoparticle by lyophilization process of a solution of polymeric nanoparticle,
   wherein the solution of polymeric nanoparticle comprises an amphiphilic block copolymer consisting of a hydrophilic block (A) and a hydrophobic block (B) in A-B, A-B-A or B-A-B form; a polylactic acid derivative having carboxyl terminal group; a lyophilization aid; and a poorly water-soluble drug which is paclitaxel or docetaxel,
   wherein the solution of polymeric nanoparticle has a polymer concentration of 120 mg/ml or lower,
   wherein the lyophilization process comprises:
   a) a first freezing step where the solution of polymeric nanoparticle is frozen to a temperature in the range of −10 to −45° C.;
   b) an annealing step where the resulting product of the first freezing is heated to a temperature in the range of −25 to 0° C.;
   c) a second freezing step where the resulting product of the annealing is frozen to a temperature in the range of −10 to −45° C.;
   d) a primary drying step where the resulting product of the second freezing is dried at a temperature of lower than 0° C. under reduced pressure;
   e) a secondary drying step where the resulting product of the primary drying is dried at a temperature of 0° C. or higher under reduced pressure; and
   f) introducing the resulting product into a vial, and sealing the vial in vacuo; and
   wherein the lyophilizate of polymeric nanoparticle is reconstituted within 5 minutes when reconstituted with an aqueous solvent under atmospheric pressure;
   the amount of the lyophilization aid is 10 to 60% by weight, based on the total dry weight of the lyophilizate of polymeric nanoparticle;
   the hydrophilic block (A) is selected from the group consisting of polyethylene glycol, monomethoxypolyethylene glycol, polyvinyl pyrrolidone, polyvinyl alcohol and polyacrylamide; and the hydrophobic block (B) is selected from the group consisting of polylactide, polyglycolide, polydioxan-2-one, polycaprolactone, polylactic-co-glycolide, polylactic-co-caprolactone, polylactic-co-dioxan-2-one and polyglycolic-co-caprolactone;
   the hydrophilic block (A) has a number average molecular weight of 500 to 50,000 Daltons; and the hydrophobic block (B) has a number average molecular weight of 500 to 50,000 Daltons;
   the polylactic acid derivative having carboxyl terminal group has a number average molecular weight of 500 to 5,000 Daltons; and
   the lyophilizate has an average pore size of 70 μm or greater.

2. The method for preparing lyophilizate of polymeric nanoparticle according to claim 1, wherein, in the lyophilization process,
   the first freezing is conducted from an initial temperature of 0 to 35° C. to a final temperature of −10 to −45° C.

with reducing the temperature for 0.5 to 24 hours followed by maintaining the temperature for 0.5 to 24 hours;

the annealing is conducted from an initial temperature of −10 to −45° C. to a final temperature of −25 to 0° C. with elevating the temperature for 0.5 to 24 hours followed by maintaining the temperature for 0.2 to 12 hours;

the second freezing is conducted from an initial temperature of −25 to 0° C. to a final temperature of −10 to −45° C. with reducing the temperature for 0.5 to 24 hours followed by maintaining the temperature for 0.5 to 24 hours;

the primary drying is conducted under a vacuum degree of 50 to 500 mTorr at a temperature of −45 to below 0° C. for 24 to 96 hours; and the secondary drying is conducted under a vacuum degree of 50 to 500 mTorr at a temperature of 0 to 50° C. for 6 to 48 hours.

3. The method for preparing lyophilizate of polymeric nanoparticle according to claim 1, wherein the hydrophilic block (A) has a number average molecular weight of 500 to 20,000 Daltons; and the hydrophobic block (B) has a number average molecular weight of 500 to 20,000 Daltons.

4. The method for preparing lyophilizate of polymeric nanoparticle according to claim 3, wherein the weight ratio of the hydrophilic block (A): the hydrophobic block (B) in the amphiphilic block copolymer is 2:8 to 8:2.

5. The method for preparing lyophilizate of polymeric nanoparticle according to claim 1, wherein the polylactic acid derivative having carboxyl terminal group is one having alkali metal ion bonded to the terminal carboxylic acid group or carboxyl group of one or more selected from the group consisting of D,L-polylactic acid, D-polylactic acid, polymandelic acid, copolymer of D,L-lactic acid and glycolic acid, copolymer of D,L-lactic acid and mandelic acid, copolymer of D,L-lactic acid and caprolactone, and copolymer of D,L-lactic acid and 1,4-dioxan-2-one.

6. The method for preparing lyophilizate of polymeric nanoparticle according to claim 1, wherein the solution of polymeric nanoparticle further comprises salt of divalent or trivalent metal ion.

7. The method for preparing lyophilizate of polymeric nanoparticle according to claim 6, wherein the divalent or trivalent metal ion is selected from the group consisting of calcium ($Ca^{2+}$), magnesium ($Mg^{2+}$), barium ($Ba^{2+}$), chromium ($Cr^{3+}$), iron ($Fe^{3+}$), manganese ($Mn^{2+}$), nickel ($Ni^{5+}$), copper ($Cu^{2+}$), zinc ($Zn^{2+}$) and aluminum ($Al^{3+}$).

8. The method for preparing lyophilizate of polymeric nanoparticle according to claim 1, wherein the lyophilization aid is selected from the group consisting of sugar, sugar alcohol, and mixtures thereof.

9. The method for preparing lyophilizate of polymeric nanoparticle according to claim 8, wherein the sugar is one or more selected from the group consisting of lactose, maltose, sucrose and trehalose; and the sugar alcohol is one or more selected from the group consisting of mannitol, sorbitol, maltitol, xylitol and lactitol.

10. The method for preparing lyophilizate of polymeric nanoparticle according to claim 1, wherein the prepared lyophilizate of polymeric nanoparticle comprises: 0.1 to 78.9% by weight of amphiphilic block copolymer; 20.0 to 98.8% by weight of polylactic acid derivative having carboxyl terminal group bonded to divalent or trivalent metal ion; and 0.1 to 20.0% by weight of poorly water-soluble drug.

* * * * *